United States Patent [19]

Kobayashi

[11] 4,318,397

[45] Mar. 9, 1982

[54] ATOMIZING APPARATUS

[75] Inventor: Takashi Kobayashi, Kasugai, Japan

[73] Assignee: Matsushita Seiko Co., Ltd., Osaka, Japan

[21] Appl. No.: 108,801

[22] Filed: Dec. 31, 1979

[51] Int. Cl.³ ............................................ A61M 11/04
[52] U.S. Cl. ........................... 128/200.21; 128/203.16; 239/138
[58] Field of Search ..................... 128/200.14, 200.15, 128/200.16, 200.18, 200.21, 203.16, 203.17, 368; 239/138, 369, 338

[56] References Cited

U.S. PATENT DOCUMENTS

| 1,931,662 | 10/1933 | Lambertus et al. | 239/138 |
| 2,288,416 | 6/1942 | O'Neill | 128/200.14 |
| 2,432,946 | 12/1947 | Theunissen | 128/200.14 |
| 2,479,967 | 8/1949 | Risch | 128/202.26 |
| 2,622,593 | 12/1952 | Peirano | 128/200.21 |
| 3,511,236 | 5/1970 | Conlin et al. | 128/368 X |

FOREIGN PATENT DOCUMENTS

| 19195 | 1/1882 | Fed. Rep. of Germany | 239/138 |
| 431081 | 6/1926 | Fed. Rep. of Germany | 128/200.21 |
| 1441382 | 10/1968 | Fed. Rep. of Germany | 128/200.21 |
| 1389559 | 1/1965 | France | 128/200.14 |
| 16475 | 6/1898 | Switzerland | 239/138 |

Primary Examiner—Henry J. Recla
Attorney, Agent, or Firm—Joseph W. Farley

[57] ABSTRACT

An atomizing apparatus comprising a steam generating unit, a steam nozzle communicating with the steam generating unit, a cup for containing a medicinal solution and a medicinal nozzle for drawing out the medicinal solution from the cup which are accommodated in a case with a top opening. A lid detachably fitting to the top opening of the case is integrally provided with a confining tube opposed to the steam nozzle. This structure eliminates the likelihood of causing burns to the user and troubles due to the condensation of steam, thus assuring safety and easy maintenance.

6 Claims, 8 Drawing Figures

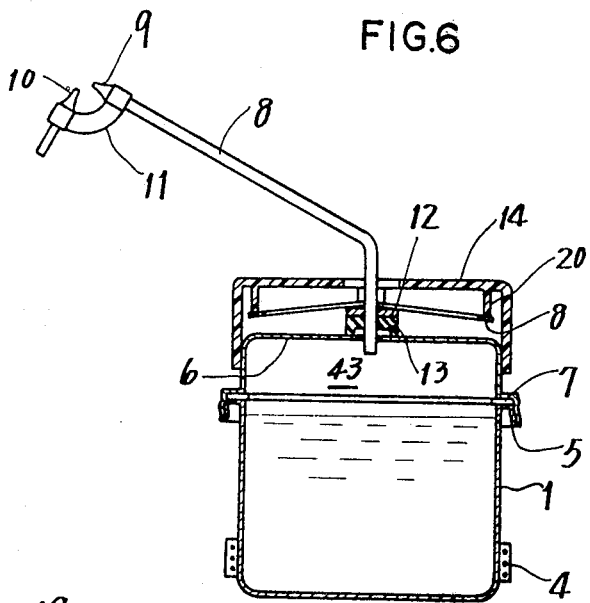
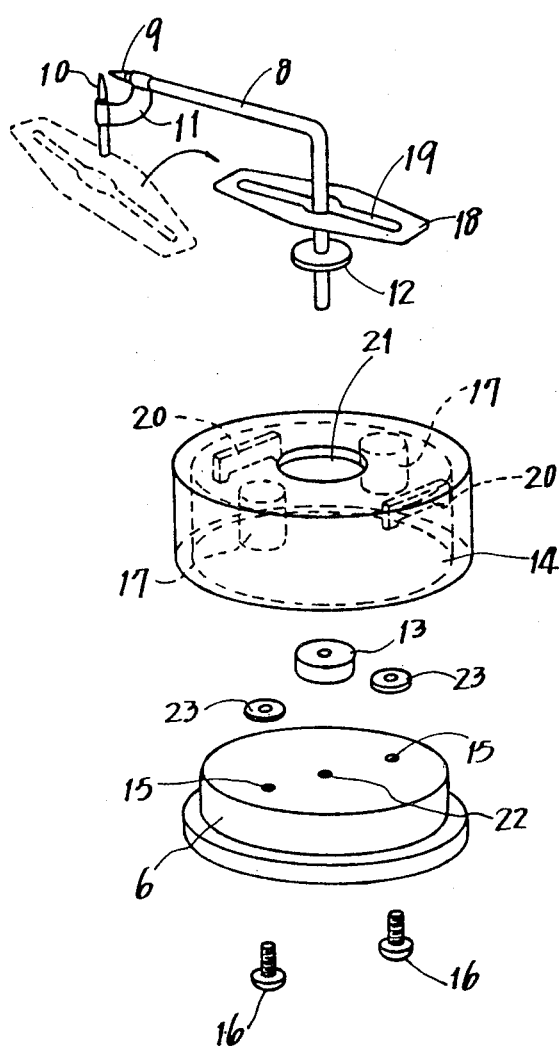

ATOMIZING APPARATUS

This invention relates to an atomizing apparatus.

Atomizing apparatus are already known in which the steam from a steam generating unit is discharged from a nozzle to draw up a medicinal solution from a cup by the Venturi effect of the jet of steam and force out a mixture of steam and atomized solution. However, the conventional atomizing apparatus involve problems as will be described later with reference to FIG. 8. The discharge nozzle is connected to the steam generating unit by an exposed metal pipe which is likely to cause a burn to the user. Condensation of steam is liable to cause troubles, or the apparatus is difficult to clean and is not sanitary.

The object of this invention is to provide an atomizing apparatus comprising a steam generating unit, a cup for containing a medicinal solution, a case housing these components and having a top opening, and a slanting lid detachably fitting to the top opening of the case and formed with a confining tube integral therewith for applying a mixture of steam and atomized medicinal solution to the throat of the human body, so that drops of water produced on the confining tube by condensation can be prevented from flowing out from the apparatus onto the table or the like on which the apparatus is placed, the lid further serving to cover the high-temperature portion of the steam channel to eliminate the likelihood of causing a burn to the user while also preventing deposition of dust or the like on the interior components.

According to a preferred embodiment, the invention provides an atomizing apparatus in which the steam to be sent to a nozzle from a steam generating unit such as a pressure tank equipped with a heater is rendered free from hot water droplets so that the throat of the human body will not be burnt with such hot water droplets to ensure high safety.

Further according to the preferred embodiment, the atomizing apparatus includes a case and a lid of the type described above which define a space, and drops of water produced by condensation on the wall surface defining the space and on the inside surface of the confining tube are adapted to flow into a water receptacle without being allowed to leak out or mingle with the medicinal solution to dilute the solution.

Other features and advantages of the invention will become apparent from the following description of the preferred embodiment with reference to the accompanying drawings, in which:

FIG. 6 is a side elevation in vertical section showing a steam generating unit and nozzles;

FIG. 7 is an exploded perspective view showing a tank cap, a cover and the nozzles.

For a better understanding of the features of the invention, the drawbacks of a conventional atomizing apparatus will be described with reference to FIG. 8 before describing the preferred embodiment of the invention with reference to FIGS. 1 to 7.

Figure 8:
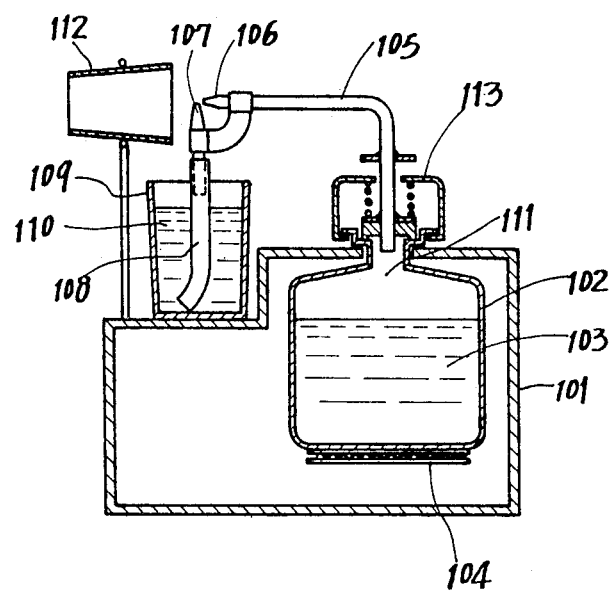
FIG. 8 is a side elevation in vertical section showing a conventional atomizing apparatus.

With the conventional atomizing apparatus shown in FIG. 8, water 103 is placed into a tank 102 housed in a case 101 and then heated by a heater 104 to produce steam, which flows through a pipe 105 and jets from a steam nozzle 106 at the forward end of the pipe 105. Disposed at a right angle with the steam nozzle 106 is a medicinal nozzle 107 connected to a tube 108 extending into a medicinal solution 110 in a cup 109. The steam jetting from the orifice of the steam nozzle 106 at a high speed produces a negative pressure in the medicinal nozzle 107 and draws up the solution 110 by virtue of a Venturi effect. Consequently the medicinal solution is mixed with the jet of steam, and the mixture is sprayed onto the throat of the human body for medication.

With such an arrangement, the quantity of water to be placed into the tank 102 is indicated usually in terms of the capacity of the tank, whereas the user is likely to fill the tank 102 with an excess of water to its opening 111 beyond the specified water level. If the apparatus is used in this state, the water, when boiled, will partially flow into the steam nozzle 106 along with steam and jet out from the nozzle 106 into a confining tube 112 in the form of hot droplets which would burn the throat of the human body.

The apparatus has another drawback. When filling the tank 102 with water, a cap 113 is removed, and water is placed into the tank through the opening 111. However, since the opening 111 is small, an excess of water will not be run off completely, or some water is likely to remain in the tank 102 when draining the tank. The remaining water will spoil or form fur on the interior of the tank. The interior of the tank is therefore difficult to keep clean and sanitary.

The conventional apparatus has still another drawback. Although the confining tube 112 is adapted to confine the emanating mixture of steam and solution to facilitate the application of the solution to the throat, the confining tube 112 is unable to completely confine the mixture, permitting the mixture to partly condense in air to droplets of water and consequently wetting the table on which the apparatus is placed.

Additionally the mixture of steam and atomized solution confined by the tube 112 will partly condense on the inside surface of the tube 112, and the resulting water will drip into the cup 109 to dilute the medicinal solution 110. As a result, the concentration of the solution decreases with the lapse of time, hence objectionable.

These drawbacks have been overcome by the present invention, the preferred embodiment of which will now be described below with reference to FIGS. 1 to 7.

A metal tank 1 having a wide top opening is supported by a heat blocking cylinder 3 made of metal. The tank 1 is provided with a heater 4 on a bottom peripheral portion thereof for heating the tank 1. The upper edge of the tank 1 at its opening is folded over to provide a threaded portion 5, which is engageable with a tank cap 6, with a packing 7 provided between the tank 1 and the cap 6 for preventing leakage of water. A metal pipe 8 has a steam nozzle 9 at its one end and an intermediate bent portion. A medicinal nozzle 10 is held by a metal bridge 11 to the steam nozzle 9 in a specified relation thereto. The pipe 8 has a seal retainer 12 close to the other end thereof. A seal 13 made from heat-resistant rubber of the silicone rubber type is mounted on the other end of the pipe 8 and bears against the retainer 12. A bowl-shaped resin cover 14 is mounted on the tank cap 6 and held thereto by screws 16 extending through holes 15 in the cap 6 and screwed into boss portions 17 on the cover 14. A plate spring 18 is formed with a slot 19 for passing the medicinal nozzle 10, bridge 11 and steam nozzle 9 therethrough. The spring 18 is engaged at its opposite ends with support portions 20 provided inside the cover 14. Indicated at 21 is a hole formed in the top plate of the cover 14 for passing the seal retainer 12 therethrough, and at 22 a hole formed in the tank cap 6 for passing the other end of the pipe 8 therethrough to hold the pipe 8 in communication with the interior of the cap 6.

The assembly described above is fabricated in the following manner. The medicinal nozzle 10, steam nozzle 9, pipe 8 and seal retainer 12 are assembled into a piece and plated, and the plated assembly is made to extend through the slot 19 of the plate spring 18 by passing the spring 18 in the broken-line position in FIG. 7 over the nozzle 10 and then over the nozzle 9 to the solid-line position shown. Since the hole 21 formed in the center of the cover 14 is larger than the seal retainer 12 and the width of the plate spring 18, the retainer 12 is passed through the hole 21 and thereafter the plate spring 18 is passed therethrough longitudinally of the spring to position the retainer 12 and the spring 18 inside the cover 14. Subsequently the seal 13 is fitted to the other end of the pipe 8 into contact with the retainer 12, and the plate spring 18 is engaged at its opposite ends with the support portions 20 on the cover 14. With packings 23 in alignment with the boss portions 17 of the cover 14 and with the holes 15 formed in the tank cap 6 for the screws 16, the cap 6 is fastened to the cover 14 with the screws 16.

Figure 5:
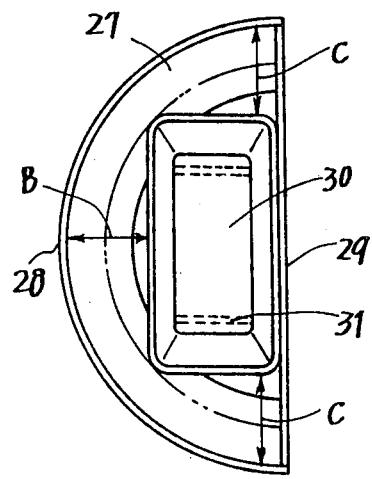
FIG. 5 is a top view of FIG. 4.

A tube 24 is connected to the medicinal nozzle 10. A case 25 has an aperture 26 in its front wall and a wide slanting opening 2 at its top and is adapted to accommodate the main body of the apparatus therein. A water receptacle 27 shaped to engage in the aperture 26 has a front wall 28 resembling one half of a truncated cone and having a sharp slant and a planar rear wall 29. A cup 30 for containing a medicinal solution is placed in the water receptacle 27. The wall of the cup 30 extends from its bottom to the desired height A at the same angle as the conical wall of the receptacle 29. This portion of the cup 30 has a rectangular cross section, and the front and rear wall thereof, as well as both side walls thereof, are symmetrical with respect to a central plane. The wall of the cup 30 extends from the point A further upward at a different angle. At the open ends of the cup 30 and the receptacle 27, the peripheral wall of the cup 30 is spaced from the front wall of the receptacle 27 by a distance B at the front and by a distance C at either side as seen in FIG. 5. The cup 30 is provided on its bottom with projections 31 for permitting the water within the receptacle 29 to freely flow under the bottom of the cup 30. A water guide 32 formed on the front wall of the case 25 inside thereof serves to guide drops of water into the receptacle 27 when the drops flow down the inner surface of the front wall. A partition plate 33 provided for a compartment for accommodating the tank 1 extends downward toward the water receptacle 27 and has an end 34 projecting into the receptacle 27. A lid 35 detachably fittable to the top opening 2 of the case 25 extends upward toward the front when positioned in place. The lid 35 is provided at a front portion thereof with a confining tube 36 integral therewith and having its lowermost end 42 positioned above the water receptacle 27 when the lid 35 is fitted in place. The case 25 has a cutout 37 for the confining tube 36 to fit in. The confining tube 36 has a stepped portion 38, by which the drops of water within the tube 36 are prevented from flowing out from the front end of the tube 36. A thermostat 39 provided on the bottom side of the tank 1 prevents overheating of the tank 1. A temperature fuse 40 is disposed under the bottom of the tank 1.

When the atomizing apparatus of the foregoing construction is to be used, the tank 1 is withdrawn from the case 25, the tank cap 6 is removed, and water is placed into the tank 1. After the tank 1 has been filled with water, water will overflow the tank, so that a specified quantity of water can be placed into the tank 1 at all times. The cap 6 is then fastened to the tank 1 with the packing 7 provided therebetween, by screwing the cap 6 on the threaded portion 5 on the outer side of the opening of the tank 1. A medicinal solution 41 is then poured into the cup 30, and the free end of the tube 24 joined to the medicinal nozzle 10 is placed into the solution 41. The top opening 2 of the case 25 is closed with the lid 35 to define a space by the case 25 and the lid 35. When the tank 1 is heated by the heater 4 in this state, the water in the tank 1 boils, whereby a steam chamber 43 formed between the cap 6 and the level of the water within the tank 1 is filled with steam. Consequently the steam flows through the pipe 8 toward the steam nozzle 9 and jets out from the nozzle 9. The solution 41 in the cup 30 is drawn up through the tube 24 and forced out from the medicinal nozzle 10 as mixed with the jet of steam by the resulting Venturi effect. The emanating mixture is confined by the tube 36 and led to the throat of the human body.

The portion of the mixture left unconfined by the tube 36 at this time remains in the space defined by the case 25 and the lid 35 and settles on the inner surfaces of the lid 35 and the case 25 in the form of drops of water, which are trapped in the water receptacle 27 without leaking out from the case 25.

With the conventional apparatus, drops of water formed by condensation on the inner surface of the confining tube will be forced forward by the jet of steam and fall off the front end of the tube onto the table or the like on which the apparatus is placed, whereas according to this invention the forwardly upward inclination of the confining tube 36 enables such drops to flow down against the stream of steam, with the stepped portion 38 also preventing drops of water from falling off the front end of the tube 36.

Figure 1:
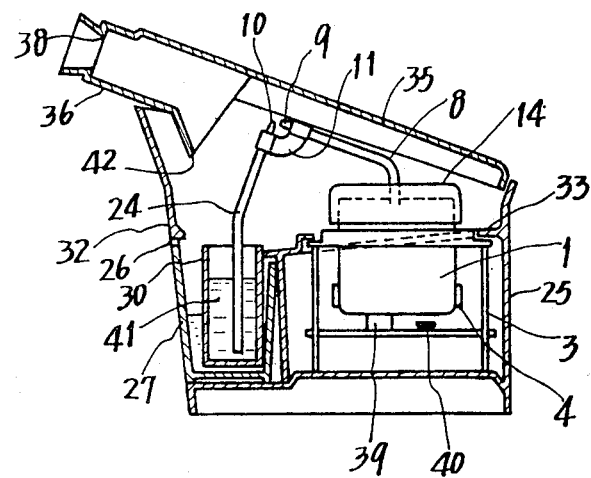
FIG. 1 is a side elevation in vertical section showing an atomizing apparatus embodying the invention.
Figure 2:
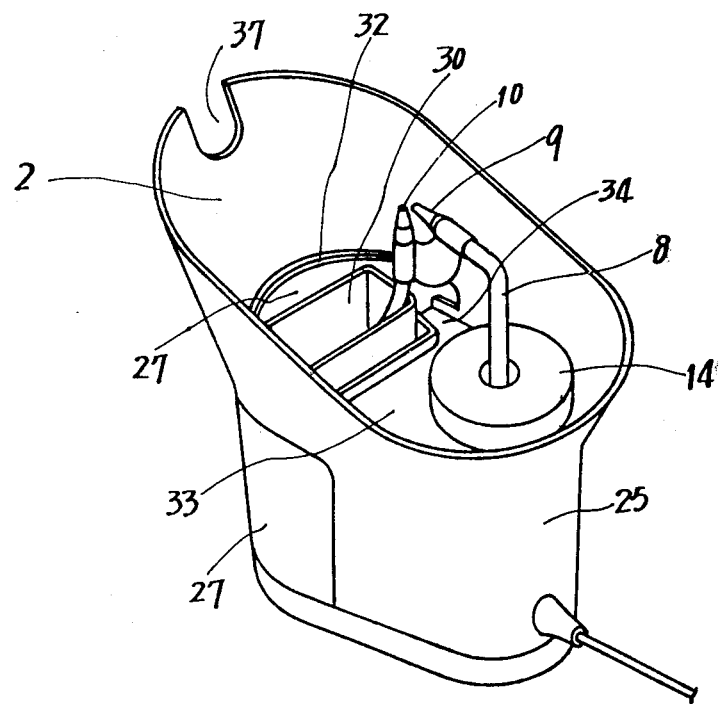
FIG. 2 is a perspective view showing the atomizing apparatus of FIG. 1 with its lid removed.
Figure 3:
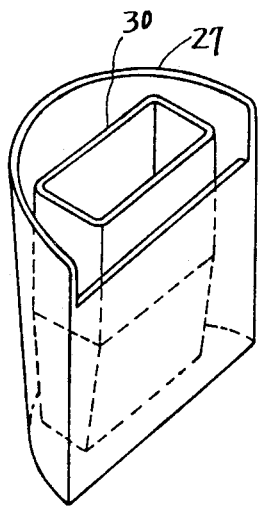
FIG. 3 is a perspective view showing a water receptacle and a cup for containing a medicinal solution.
Figure 4:
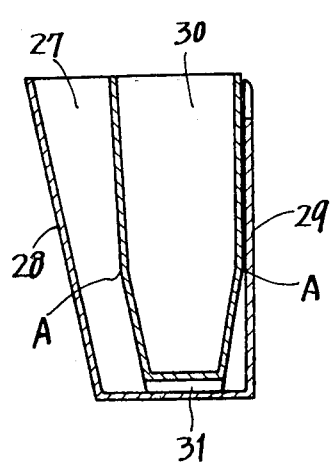
FIG. 4 is a side elevation in vertical section showing the cup as placed in the water receptacle.

As will be apparent from FIG. 1, the pipe 8, steam nozzle 9, bridge 11 and medicinal nozzle 10 will have a high temperature during operation. If the apparatus is used with these high-temperature portions exposed, namely, in the absence of the confining tube 36, the atomized medicinal solution as entrained in the stream of steam will spread out and is not applicable as contemplated. Since the confining tube 36 is integral with the lid 35, the lid 35 is therefore installed in place invariably when the atomizing apparatus is used.

Accordingly the apparatus is usable with extreme safety because the high-temperature portions are in no way accessible during use. When the water within the tank has completely evaporated off during use for a prolonged period of time, the case 25 made of synthetic resin will be subjected to the hazard of an abrupt increase in the temperature of the tank 1 and intense radient heat despite the presence of the heat blocking cylinder 3, so that the thermostat 39 and the temperature fuse 40 are provided as a double safety means for preventing overheating. The case 25 and the lid 35, which wholly cover the main components of the apparatus, keep them free from dust and sanitary, while when the lid 35 is removed, the interior can be cleaned easily through the wide top opening of the case for sanitation.

The mixture of steam and atomized medicinal solution overflowing the confining tube 36 fills the space defined by the case 25 and lid 35 and condenses to drops, which flow down the partition plate 33 slanting downward toward the water receptacle 27 and fall into the receptacle through the clearances C formed between the cup 30 and the receptacle 27. The drops of mixture or water flowing down the inner surface of the front wall the case 25 pass over the water guide 32 and fall into the receptacle 27 through the clearance B between the cup 30 and the receptacle wall. The drops of mixture or water formed by condensation on the inner surface of the confining tube 36 fall into the water receptacle 27 from the lowermost end 42 of the tube which end is positioned above the clearance B. Accordingly the water resulting from condensation will not fall into the cup 30 to dilute the medicinal solution 41, permitting the solution to retain the same concentration during medication. The medicinal solution is thus rendered free from the drops of water and can therefore be kept sanitary.

What is claimed is:

1. An atomizing apparatus comprising:
    a case having an open top, a rear wall and a front wall;
    a steam generating unit provided in the case adjacent the rear wall thereof;
    a cup arranged in the case for containing a medicinal solution;
    a steam nozzle communicating with the steam generating unit and having a discharge end directed in a discharge path extending toward and above the front wall;
    a medicinal nozzle communicating with the cup and having a discharge end close to the discharge end of the steam nozzle for drawing out the medicinal solution from the cup;
    a water receptacle disposed in the case adjacent the front wall thereof;
    a lid detachably fitting on the case to cover the steam generating unit, the cup, the steam nozzle, the medicinal nozzle and the water receptacle, the lid being integrally provided with a confining tube arranged forwardly and in the discharge path of the steam nozzle;
    a water guide provided inside of the case and positioned over the water receptacle; and
    a partition plate provided in the case below the lid and extending forwardly and downwardly from the rear wall toward the front wall of the case and having an end positioned in communication with the water receptacle, the partition plate together with the water guide serving to guide drops of water formed on the interior wall surfaces of the case and lid into the water receptacle.

2. An apparatus as defined in claim 1 wherein the steam generating unit comprises a tank having a wide top opening and a tank cap separate from the tank and detachably mountable on the tank to form a steam chamber between the tank and the cap even when the tank is full of water.

3. An apparatus as defined in claim 1 wherein the cup is disposed within the water receptacle with a clearance formed between the peripheral wall of the cup and the peripheral wall of the water receptacle so that the drops of water are allowed to fall into the water receptacle through the clearance.

4. An apparatus as defined in claim 3 wherein the confining tube has its lowermost end positioned above the clearance, whereby the drops of water on the inside surface of the confining tube are allowed to fall into the water receptacle.

5. An apparatus as defined in claim 1 wherein the confining tube has inside thereof an inwardly projecting stepped portion to prevent drops of water formed by condensation on the inner surface of the confining tube from flowing out of the tube.

6. An apparatus as defined in claim 5 wherein the confining tube has its lowermost end positioned above the water receptacle, whereby drops of water on the inner surface of the confining tube are allowed to fall into the water receptacle.

* * * * *